United States Patent [19]

Fayerman et al.

[11] Patent Number: 4,666,846
[45] Date of Patent: May 19, 1987

[54] NOVEL CLONING VECTORS CONTAINING SELECTABLE GENETIC MARKERS FOR USE IN STREPTOMYCES AND RELATED ORGANISMS

[75] Inventors: Jeffrey T. Fayerman; Michael D. Jones, both of Indianapolis, Ind.; Nancy E. Malin, Mountain View, Calif.

[73] Assignee: Eli Lilly and Company, Indianapolis, Ind.

[21] Appl. No.: 581,396

[22] Filed: Feb. 17, 1984

[51] Int. Cl.[4] .................... C12N 1/00; C12N 15/00; C12N 1/20; C12P 21/00; C12P 21/02; C12P 21/04; C12P 19/34; C07H 21/04

[52] U.S. Cl. .................... 435/243; 435/68; 435/70; 435/71; 435/91; 435/172.3; 435/317; 435/253; 536/27; 935/6; 935/29; 935/75

[58] Field of Search ............... 435/68, 70, 71, 91, 435/172.3, 317, 253, 243, 886; 536/27; 935/24, 75, 6

[56] References Cited

U.S. PATENT DOCUMENTS 4,416,994 11/1983 Nakatsukasa et al. ............... 935/75

OTHER PUBLICATIONS

Jones et al, "pFJ269, A New Plasmid Isolated from a Beta-Lactam Antibiotic Producing Streptomycete", Chem. Abstr., 102:56905r (1985) of J. Antibiotic. 37(12), 1727, Dec. (1984).
Soberon et al, "Construction and Characterization of New Cloning Vehicles., IV., Deletion Derivatives of pBR322 and pBR325", Chem. Abstr., 93:65765t (1980) of Gene 9:287 (1980).
American Type Culture Collection Catalogue of Strains I, Fifteenth Edition, 1982, p. 259.
Thompson, C. et al., 1980 Nature 286:525.
Hopwood, D. A. et al., 1983, Trends in Biotechnology, 1:42.
Katz, E. et al., 1983, J. Gen. Microbiol., 129:1703.
Richardson, M. et al., 1982, Gene 20:451.

Primary Examiner—James Martinell
Attorney, Agent, or Firm—Lisabeth Feix Murphy

[57] ABSTRACT

The present invention discloses novel recombinant DNA cloning vectors for use in Streptomyces and related organisms. These novel cloning vectors contain genetic markers that provide antibiotic resistance or colorimetric selectivity to the host cells. The invention further comprises transformants of the aforementioned vectors.

20 Claims, 9 Drawing Figures

Restriction Site and Function Map of
Plasmid pFJ301
(13.7 kb)

Figure 1

Restriction Site and Function Map of
Plasmid pFJ301
(13.7 kb)

Figure 2:
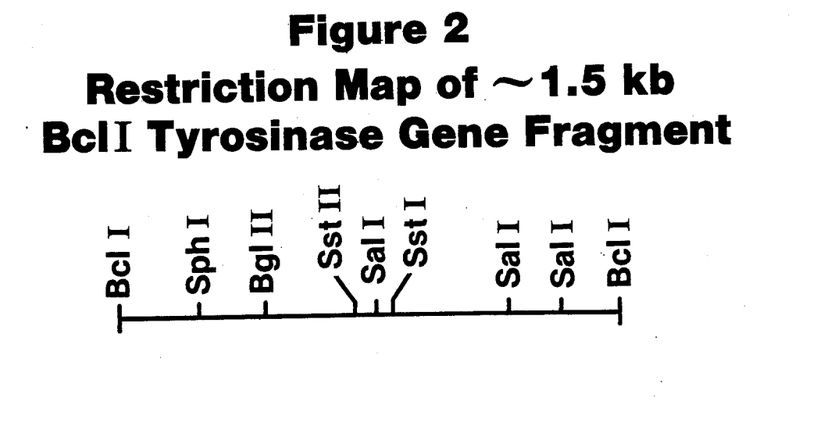

Figure 2
Restriction Map of ~1.5 kb
BclI Tyrosinase Gene Fragment

Figure 3:
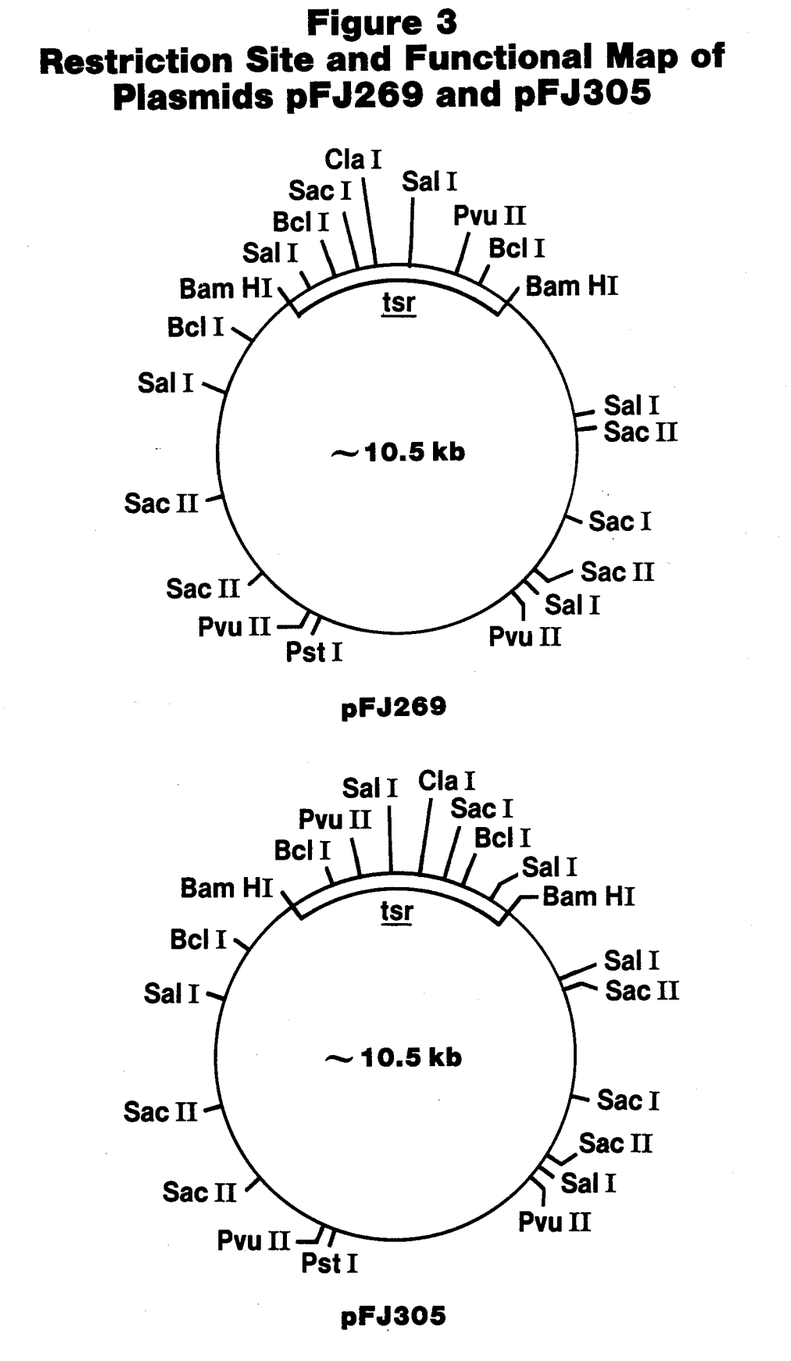

Figure 3
Restriction Site and Functional Map of Plasmids pFJ269 and pFJ305 pFJ269 pFJ305

Figure 4:
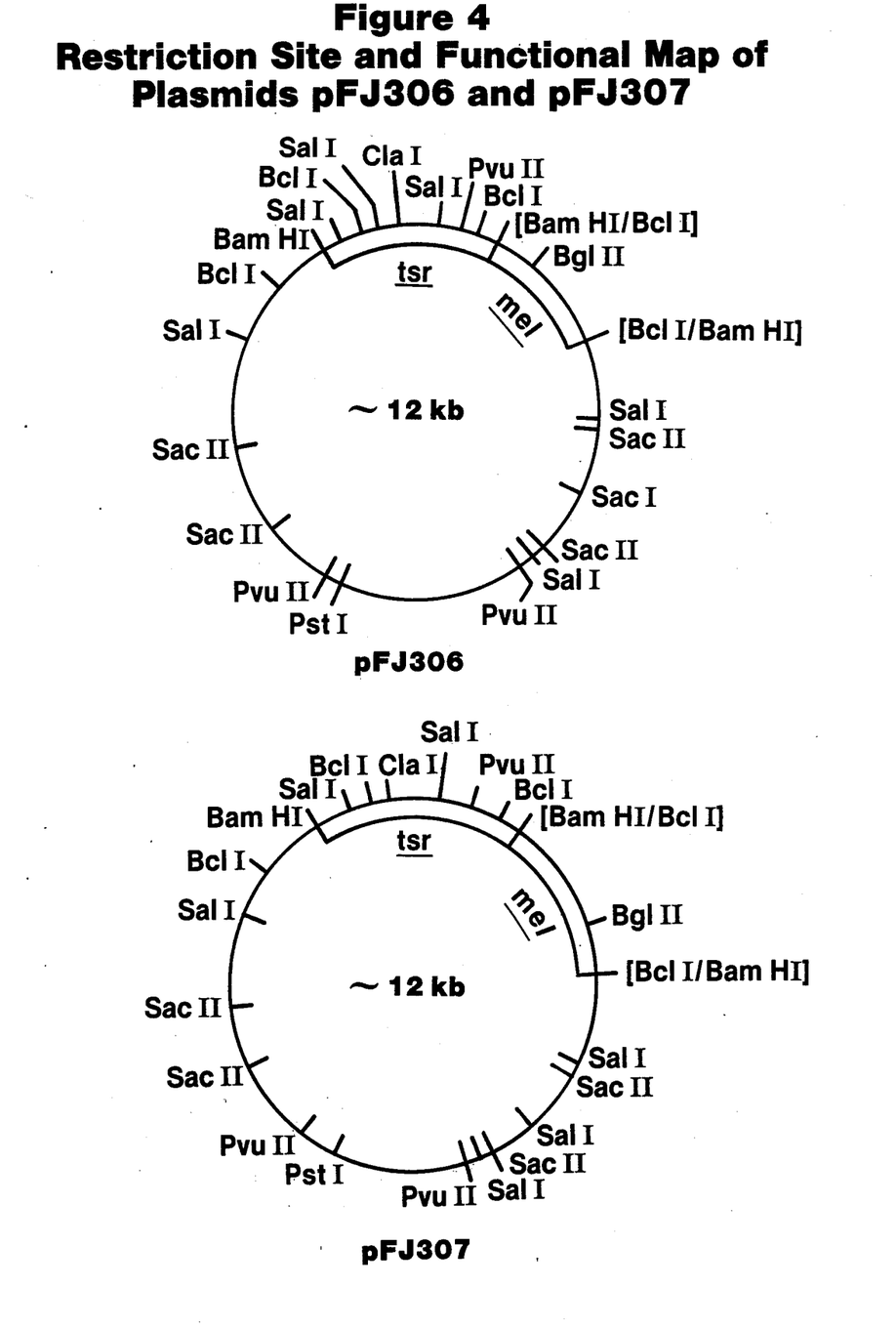

Figure 4
Restriction Site and Functional Map of Plasmids pFJ306 and pFJ307 pFJ306 pFJ307

Figure 5:
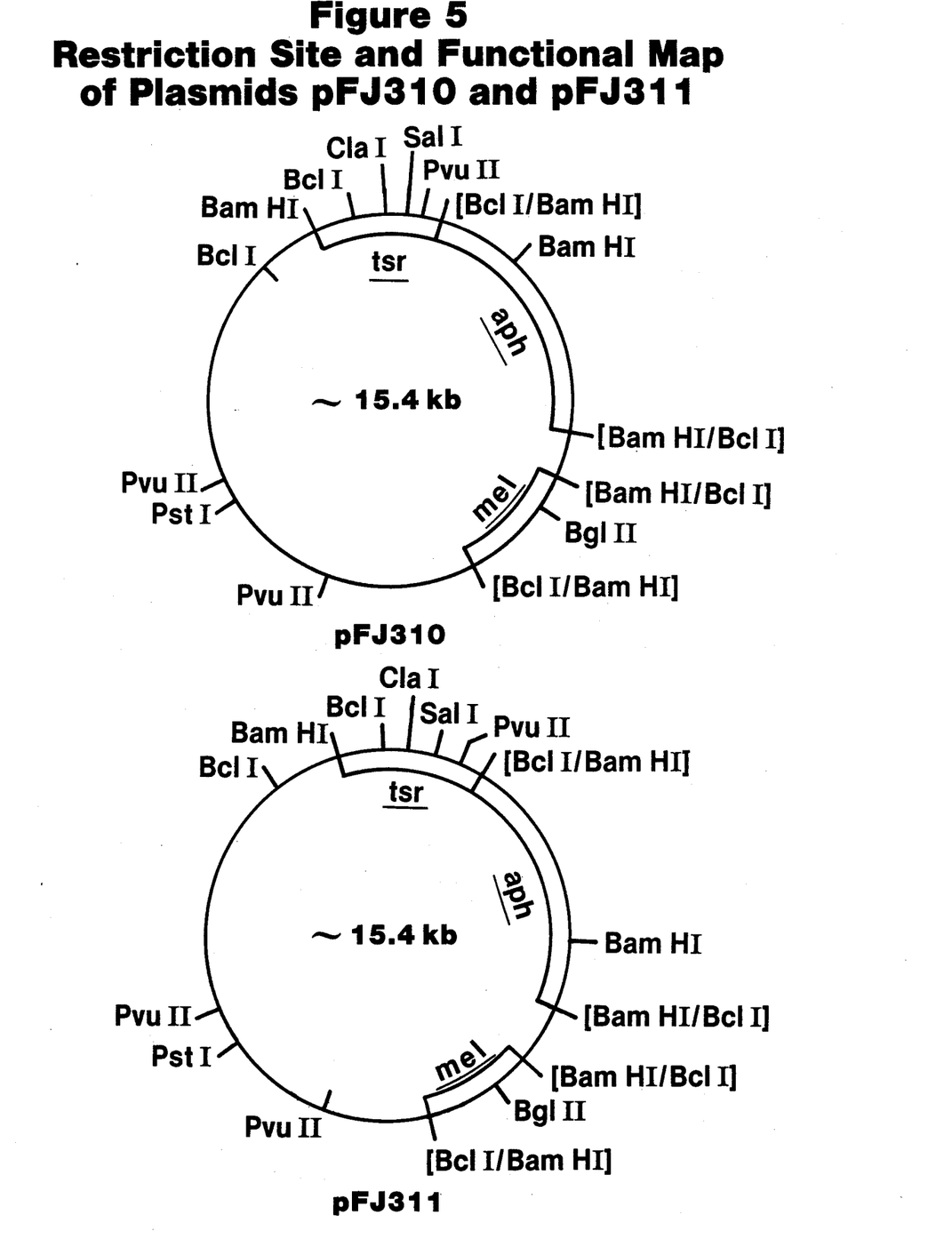

Figure 5
Restriction Site and Functional Map of Plasmids pFJ310 and pFJ311

Figure 6:
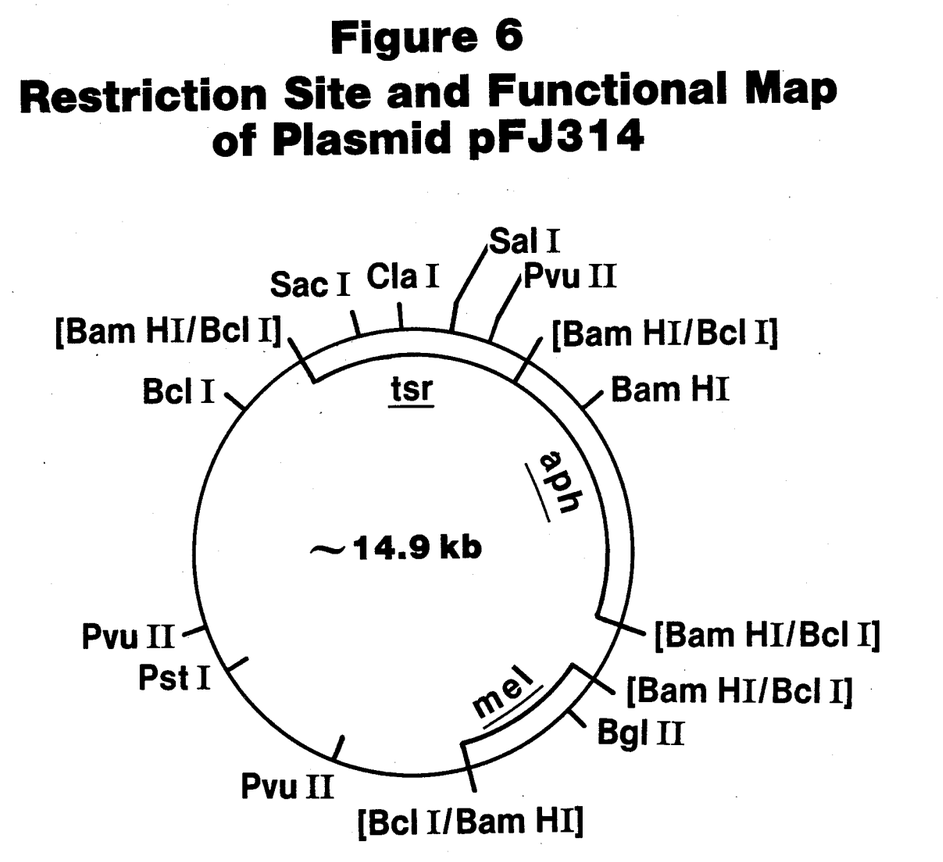

**Figure 6
Restriction Site and Functional Map
of Plasmid pFJ314**

Figure 7:
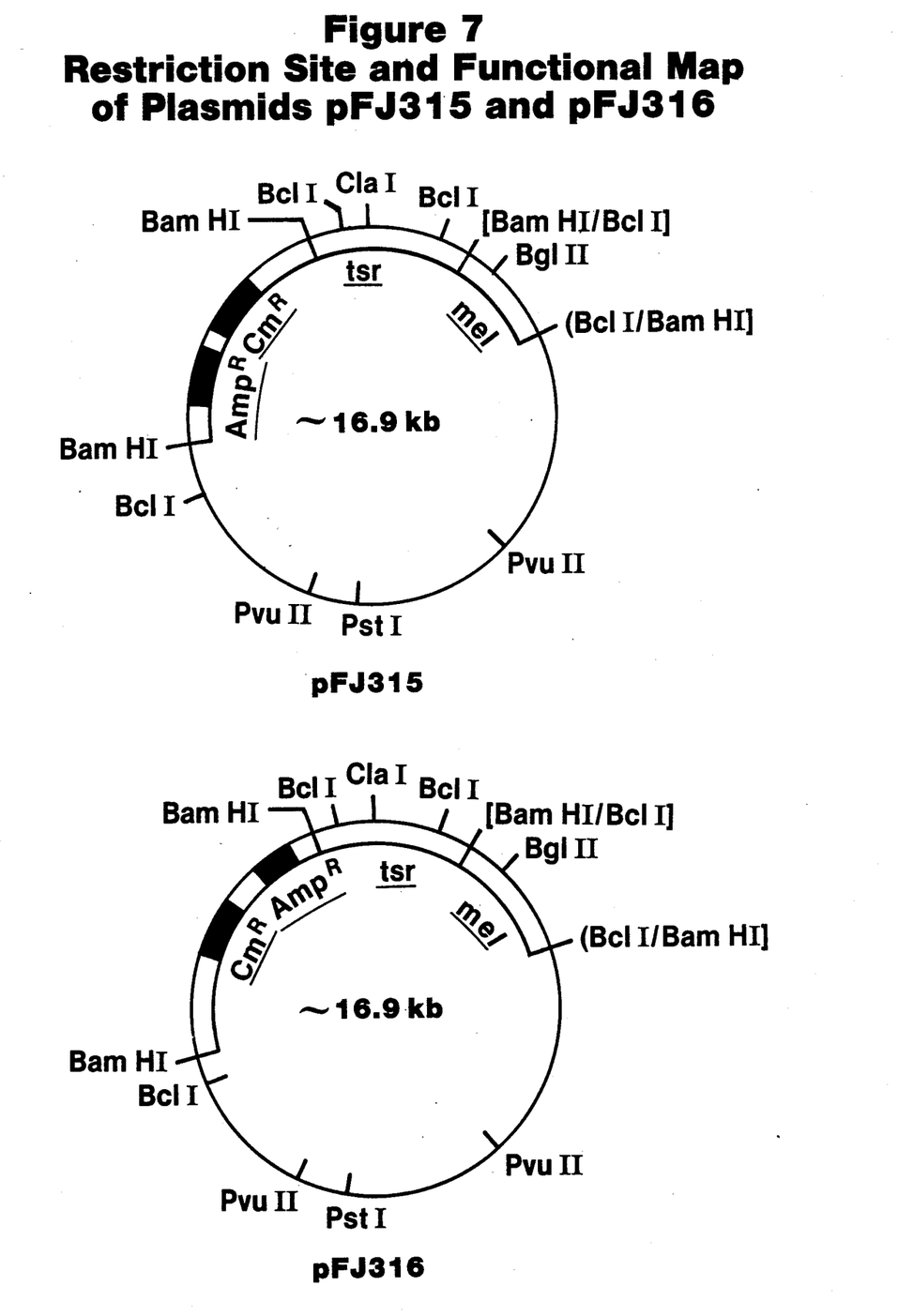

Figure 7
Restriction Site and Functional Map of Plasmids pFJ315 and pFJ316 pFJ315 pFJ316

Figure 8:
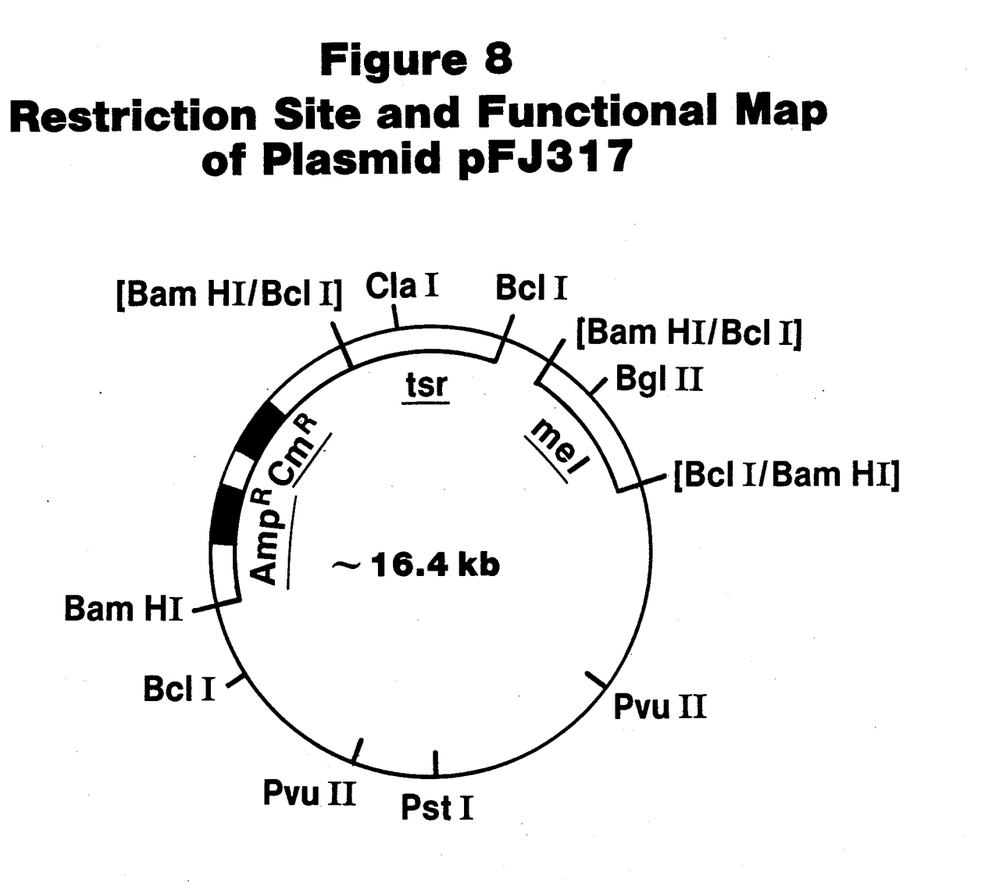

Figure 8
Restriction Site and Functional Map of Plasmid pFJ317

Figure 9:
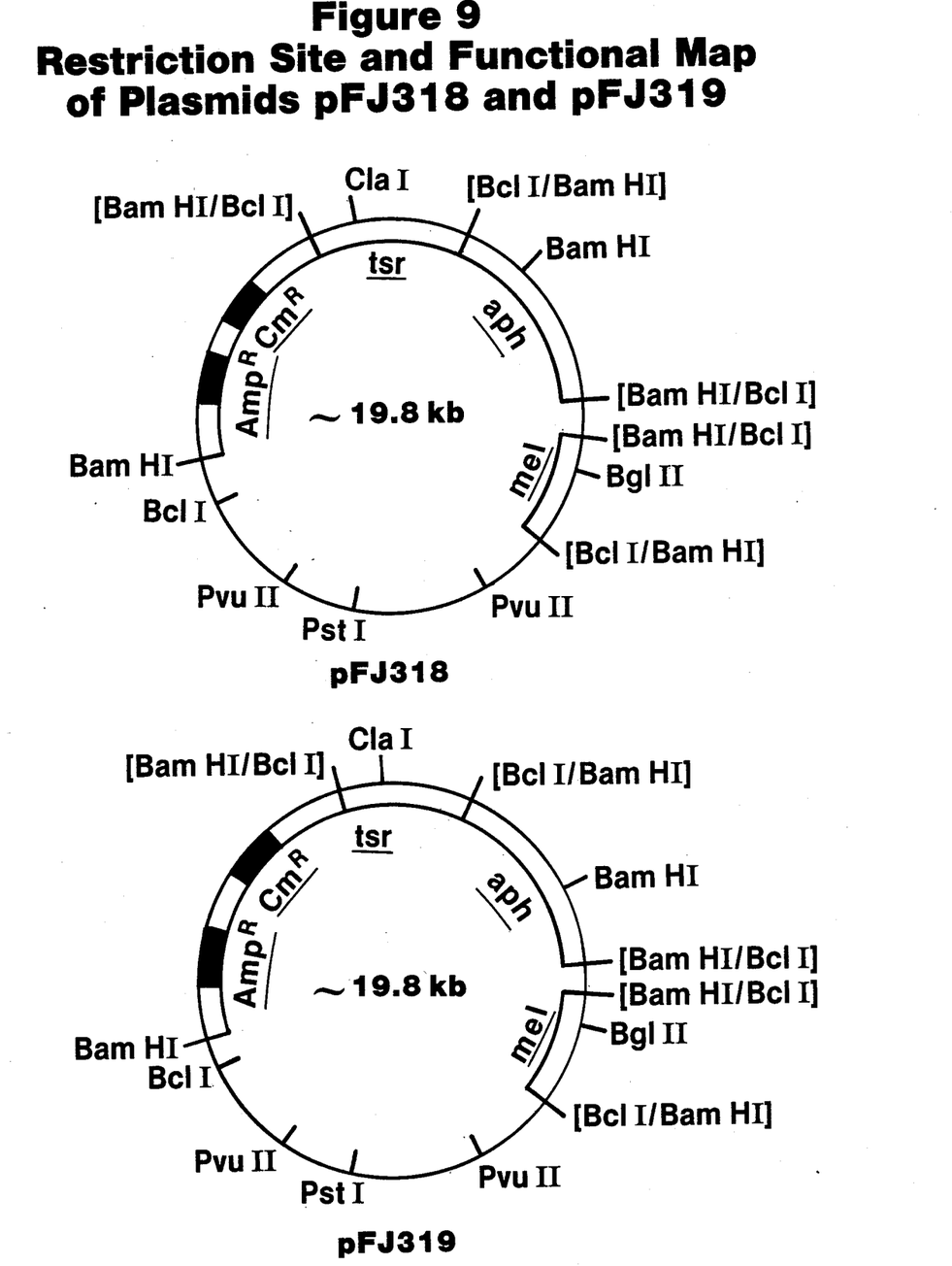

Figure 9
Restriction Site and Functional Map
of Plasmids pFJ318 and pFJ319 pFJ318 pFJ319

NOVEL CLONING VECTORS CONTAINING SELECTABLE GENETIC MARKERS FOR USE IN STREPTOMYCES AND RELATED ORGANISMS

SUMMARY OF THE INVENTION

The present invention comprises novel recombinant DNA cloning vectors comprising a functional Streptomyces origin of replication-containing restriction fragment of plasmid pFJ301 and one or more DNA segments that provide selectable genetic markers. The invention further comprises transformants of the aforementioned vectors.

The present invention provides antibiotic resistance conferring or colorimetric selectable cloning vectors for use in Streptomyces and related host cells. Heretofore, the development and explcitation of recombinant DNA technology in the above organisms has been retarded and made especially difficult because of the general lack of selectable genetic markers on cloning vectors. The vectors of the present invention are functional and selectable in both Streptomyces and other host strains and therefore represent a significant advance in the technical art.

The present vectors are particularly useful because they are relatively small, versatile, and can transform and be selected in any Streptomyces cell that is sensitive to an antibiotic for which resistance is conveyed or is capable of expressing a colorimetric phenotype. Since more than seventy percent of naturally occurring antibiotics are produced by Streptomyces strains, it is desirable to develop cloning systems and vectors that are applicable to that industrially important group. The present invention provides such vectors and thus allows for the cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the billions of cells, has acquired the plasmid DNA. This is important because DNA sequences that are themselves non-selectable can be inserted into the vectors and, upon transformation, cells containing the vector and the particular DNA sequence of interest can be isolated either by appropriate antibiotic selection or colorimetric assay analysis.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a stable and heritable change in the recipient cell.

Transformant—a recipient host cell that has undergone transformation.

Sensitive Host Cell—a host cell that cannot grow in the presence of a given antibiotic without a DNA segment that confers resistance thereto or a host cell capable of expressing a gene conferring a colorimetric phenotype.

Restriction Fragment—any linear DNA generated by the action of one or more restriction enzymes.

Genetic Marker—a gene or combination of genes of known function and location on a chromosome or recombinant DNA cloning vector.

Amp$^R$—the ampicillin resistant phenotype.
Cm$^R$—the chloramphenicol resistant phenotype.
Tet$^S$—the tetracycline sensitive phenotvpe.
tsr—the thiostrepton resistant phenotype.
aph—the neomycin resistant phenotype.
mel+—the melanin producing phenotype.

DETAILED DESCRIPTION OF THE INVENTION

The present invention comprises recombinant DNA cloning vectors comprising:
(a) a functional Streptomyces origin of replication-containing restriction fragment of plasmid pFJ301, and
(b) one or more DNA segments that convey resistance to at least one antibiotic or that convey colorimetric selectivity when transformed into a sensitive restrictionless host cell.

The invention further comprises transformants of the aforementioned vectors.

Figure 1:
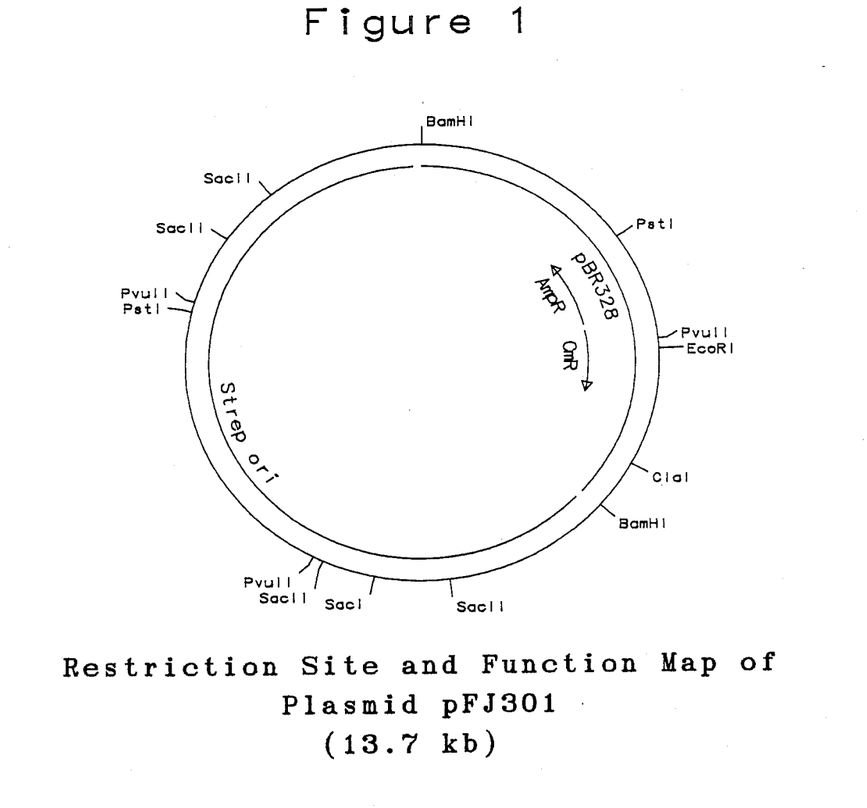

The vectors of the present invention are constructed by ligating one or more antibiotic resistance-conferring DNA segments or colorimetric gene-containing DNA fragments into a Streptomyces origin of replication-containing restriction fragment of plasmid pFJ301. Plasmid pFJ301, from which the origin of replication-containing restriction fragments are obtained, is approximately 13.7 kb and contains several restriction sites which are particularly advantageous for molecular cloning. Since the Streptomyces origin of replication of plasmid pFJ301 has been localized to within the ~8.8 kb BamHI restriction fragment, a variety of different origin of replication containing fragments can be generated by digesting the plasmid with restriction enzymes that cut outside the ~8.8 kb BamHI region. A detailed restriction site map of plasmid pFJ301 is presented in FIG. 1 of the accompanying drawings. The restriction endonuclease abbreviations shown in the drawings are standard and well-known in the art. For purposes of the present application, FIG. 1 and all subsequent figures are not drawn to scale.

Plasmid pFJ301 can be conventionally isolated from Escherichia coli K12 HB101/pFJ301, a strain deposited and made part of the permanent stock culture collection of the Northern Regional Research Laboratory, Peoria, Ill. The strain is available to the public, as a preferred source and stock reservoir of the plasmid, under the accession number NRRL B-15724.

Although many different Streptomyces origin of replication-containing fragments of plasmid pFJ301 can be constructed, the fragment exemplified herein for illustrative purposes is the ~8.8 kb BamHI restriction fragment. This fragment can be independently ligated to one or more antibiotic resistance-conferring DNA fragments or colorimetric gene-containing DNA fragments, exemplified herein for illustrative purposes by the thiostrepton resistance-conferring ~1.6 kb BamHI restriction fragment of plasmid pLR2, the neomycin resistance-conferring ~3.4 kb BamHI restriction fragment of plasmid pLR1, and the ~1.5 kb BclI tyrosinase gene-containing fragment of plasmid pIJ702, to form vectors illustrative of the present invention.

Plasmids pLR2 and pLR1, respective sources of the thiostrepton and neomycin resistance-conferring fragments, are constructed in accordance with U.S. Pat. No. 4,416,994. Plasmid pIJ702 (ATCC 39155) is the source of the tyrosinase gene-containing DNA fragment which is responsible for melanin synthesis and produces a mel+ phenotype in its host organism. The expression of a mel+ phenotype is both strain and media dependent. For example, when *Streptomyces lividans* colonies are plated on tryptic soy agar (available from Difco Laboratories, P.O. Box 1058A, Detroit, Mich. 48232), the mel+ phenotype is expressed as a black pigment releasing colony. Thus, this assay provides for the convenient selection of transformants. A linear restriction map of the ~1.5 kb BclI fragment is presented in FIG. 2 of the accompanying drawings.

For convenience and ease of construction the thiostrepton resistance-conferring ~1.6 kb BamHI fragment, the neomycin resistance-conferring ~3.4 kb BamHI fragment, and the ~1.5 kb BclI tyrosinase gene-containing fragment are ligated to the ~8.8 kb BamHI origin of replication-containing fragment of plasmid pFJ301. The resulting recombinant DNA is then ligated to produce plasmids illustrative of the present invention. Thus, ligation of the ~1.6 kb BamHI fragment of plasmid pLR2 into the ~8.8 kb BamHI fragment of plasmid pFJ301 results in illustrative plasmids pFJ269 and pFJ305. Additionally, ligation of the ~1.5 kb BclI fragment of plasmid pIJ702 into either BamHI restriction site of plasmid pFJ269 results in illustrative plasmids pFJ306, pFJ307, pFJ308, and pFJ309. Similarly, ligation of the ~3.4 kb BamHI fragment of plasmid pLR1 into either of the two BclI restriction sites contained within the thiostrepton resistance gene of plasmid pFJ306 results in illustrative plasmids pFJ310, pFJ311, pFJ312, and pFJ313.

Recombinant plasmids of four orientations may result depending upon (1) the orientation of the particular antibiotic resistance-conferring DNA fragment or colorimetric gene-containing DNA fragment and (2) the point of insertion of the aforementioned fragments at one of two non-essential BamHI or two non-essential BclI restriction sites of plasmids pFJ269 and pFJ305.

The ligations used to construct illustrative plasmids pFJ306 and pFJ307 are made possible by the fact that some restriction enzymes, such as BclI and BamHI, generate compatible cohesive ends. However, in a few cases, fragments generated by one restriction enzyme when ligated to fragments generated by a second enzyme give rise to recombinants that are recognized by neither of the parental enzymes. For example, when fragments generated by BclI (T ↓ GATCA) are ligated to fragments generated by BamHI (G ↓ GATCC), the resulting recombinant target sites, hereinafter designated as [BclI/BamHI] or [BamHI/BclI], are cleaved by neither BclI nor BamHI.

Thus, although these target sites are nonfunctional for subsequent restrictions, this construction may generate a unique BamHI or BclI restriction site useful for subsequent restrictions.

Various plasmid pFJ301 restriction fragments can be used for the ligation to antibiotic resistance-conferring DNA segments provided that the Streptomyces origin of replication contained in the ~8.8 kb BamHI restriction fragment is present. Additional plasmid pFJ301 restriction fragments, useful for constructing illustrative plasmids within the scope of the present invention, include, but are not limited to, the PstI and EcoRI fragments. A particular antibiotic resistance-conferring DNA segment or colorimetric gene-containing DNA segment is not limited to a single position on a plasmid pFJ301 fragment but can be ligated or inserted into varying sites provided that the origin of replication or other necessary plasmid contained physiological functions are not disrupted. Those skilled in the art understand or can readily determine which sites are advantageous for the ligation or insertion of a particular DNA segment.

Although the thiostrepton and neomycin antibiotic resistance-conferring DNA segments exemplified herein are respectively the ~1.6 kb and ~3.4 kb BamHI restriction fragments of plasmids pLR2 and pLR1, those skilled in the art can construct and use, either individually or in combination, additional DNA segments that also confer resistance to thiostrepton and neomycin. Additional thiostrepton resistance-conferring DNA segments of plasmid pLR2 include, for example, the ~13 kb PstI restriction fragment and the ~0.8 kb BclI restriction fragment. Additional neomycin resistance-conferring DNA segments of plasmid pLR1 include, for example, the ~3.5 kb PstI restriction fragment and also the larger of the SstI-KpnI fragments of the ~3.4 kb BamHI restriction fragment.

Still other DNA segments that confer resistance to the same or to different antibiotics such as, for example, chloramphenicol, streptomycin, hygromycin, puromycin, viomycin, tylosin, erythromycin, vancomycin, actaplanin, and the like can also be constructed and used by those skilled in the art.

Functional derivatives of the various antibiotic resistance-conferring DNA segments or colorimetric gene-containing DNA segments can be made by adding, eliminating, or substituting certain nucleotides in accordance with the genetic code. Those skilled in the art will understand that ligation of these modified segments, or any other antibiotic resistance-conferring DNA segment or colorimetric gene-containing DNA segment, to an origin of replication-containing fragment of plasmid pFJ301 results in vectors that are also within the scope of the present invention.

Derivative vectors that further exemplify the invention can also be constructed. For example, BamHI-BclI deletion of plasmid pFJ315 results in illustrative plasmid pFJ317, a plasmid from which additional derivatives can also be made. Thus, insertion of the plasmid pLR1 ~3.4 kb BamHI neomycin resistance-conferring fragment into plasmid pFJ315 results in illustrative plasmids pFJ318 and pFJ319. The aforementioned antibiotic resistance-conferring and colorimetric gene-containing derivative plasmids contain the plasmid pFJ301 origin of replication and are therefore within the scope of the present invention.

The present Streptomyces-functional vectors such as, for example, plasmid pFJ269, pFJ305, pFJ306, pFJ307, pFJ308, pFJ309, pFJ310, pFJ311, pFJ312, pFJ313, and pFJ314 can be ligated to a functional replicon-containing and antibiotic resistance-conferring restriction fragment of a variety of *E. coli* plasmids such as, for example, plasmids pBR322, pBR325, pBR328 and the like, to produce self-replicating bifunctional vectors that are selectable in both *E. coli* and Streptomyces.

These bifunctional constructions comprise the pFJ301 Streptomyces origin of replication, a DNA segment that confers antibiotic resistance or colorimetric gene-selectivity in Streptomyces, a replicon that is functional in *E. coli* and also a DNA segment that confers antibiotic resistance in *E. coli*. Bifunctional constructions, exemplified herein by plasmids pFJ315, pFJ316, pFJ317, pFJ318, and pFJ319 are particularly advantageous because amplification and manipulation of plasmids can be done faster and more conveniently in *E. coli* than in Streptomyces. Thus, after desired recombinant DNA procedures are accomplished within the *E. coli* host system, the entire plasmid or particular Streptomyces DNA can be removed, and re-constructed (if necessary) to plasmid form, and then transformed into a Streptomyces or related host cell.

The recombinant DNA cloning vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether, and glycopeptide antibiotics and the like. Such restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S.. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present vectors are especially useful and can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present vectors are especially useful and can be transformed, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vectors are especially useful and can be transformed, include restrictionless cells of, for example: *S. orientalis* and *S. haranomachiensis* (vancomycin); *S. candidus* (A-35512, avoparcin), *S. eburosporeus* (LL-AM 374), and *S. toyocaensis* (A47934).

Preferred host cells of other Streptomyces restrictionless strains in which the present vectors are especially useful and can be transformed, include restrictionless cells of, for example: *S. coelicolor, S. granuloruber, S. roseosporus, S. lividans, S. tenebrarius, S. acrimycins, S. glaucescens, S. parvilin, S. pristinaespiralis, S. violaceoruber, S. vinaceus, S. virginiae, S. espinosus,* and *S. azureus.*

In addition to the representative Streptomyces host cells described above, the present vectors are also useful and can be transformed into cells of restrictionless strains of other taxa such as, for example: Bacillus, Staphylococcus and related Actinomycetes, including Streptosporangium, Actinoplanes, Nocardia, and Micromonospora. Thus, the vectors of the present invention have wide application and are useful and can be transformed into host cells of a variety of organisms.

While all the embodiments of the present invention are useful, some of the present recombinant DNA cloning vectors and transformants are preferred. Accordingly, preferred vectors are plasmids pFJ269, pFJ305, pFJ306, and pFJ318; and preferred transformants are *Streptomyces ambofaciens*/pFJ269, *S. ambofaciens*/pFJ305, *S. ambofaciens*/pFJ306, *E. coli* K12 HB101/pFJ318, and *S. ambofaciens*/pFJ318. Moreover, of this preferred group, plasmids pFJ269 and pFJ305, and transformants *S. ambofaciens*/pFJ269 and *S. ambofaciens*/pFJ305 are most preferred.

The recombinant DNA cloning vectors and transformants of the present invention have broad utility and help fill the need for suitable cloning vehicles for use in Streptomyces and related organisms. Moreover, the ability of the present vectors to confer resistance to antibiotics that are toxic to non-transformed host cells, also provides a functional means for selecting transformants. This is important because of the practical necessity for determining and selecting the particular cells that have acquired vector DNA. Additional DNA segments, that lack functional tests for their presence, can also be inserted in the present vectors and then transformants containing the non-selectable DNA can be isolated by appropriate colorimetric or antibiotic selection. Such non-selectable DNA segments can be inserted at any site, except within regions necessary for plasmid function, maintainance, and replication, and include, but are not limited to, genes that specify antibiotic modification enzymes, antibiotic resistance, antibiotic biosynthesis, and regulatory genes of all types.

More particularly, a non-selectable DNA segment that comprises a gene can be inserted in a plasmid such as for example, illustrative plasmid pFJ314, at the unique internal BamHI restriction site of the $\sim$3.4 kb BamHI neomycin resistance-conferring fragment. Such an insertion inactivates the neomycin resistance gene and thus allows for the easy identification of transformants containing the recombinant plasmid. This is done by first selecting for thiostrepton resistance and then identifying those thiostrepton resistant transformants that are not resistant to neomycin. In a similar manner, insertion of a DNA segment of interest at, for example, the unique BglII restriction site of the $\sim$1.5 kb BclI tyrosinase gene-containing fragment inactivates the tyrosinase gene. Thus, transformants carrying this recombinant plasmid also are identified easily by first selecting for thiostrepton resistance and then identifying those thiostrepton resistant transformants that do not exhibit a mel$^+$ phenotype. Therefore, the ability to select for either antibiotic resistance or colorimetric phenotypes in Streptomyces and related cells allows for the efficient isolation of the extremely rare cells, out of billions of cells, that contain the particular non-selectable DNA of interest.

The functional test for antibiotic resistance or assay for colorimetric activity, as described herein above, is also used to locate DNA segments that act as control or biosynthetic elements and direct expression of antibiotic resistance genes. Such segments, including but not limited to, promoters, attenuators, repressors, inducers, ribosomal binding sites, and the like, are used to control the expression of other genes in cells of Streptomyces and related organisms.

The antibiotic resistance-conferring and colorimetric gene-containing vectors of the present invention are also useful for insuring that linked DNA segments are stably maintained in host cells over many generations. These genes or DNA fragments, covalently linked to the thiostrepton or neomycin resistance-conferring fragment and propagated either in Streptomyces or in the cells of related organisms, are maintained by exposing the transformants to levels of thiostrepton or neomycin that are toxic to non-transformed cells. Therefore, transformants that lose the vector, and consequently any covalently linked DNA, cannot grow and are eliminated from the culture. In the case of the tyrosinase gene-containing fragments, transformants containing the linked DNA segments will produce a pigment allowing a convenient means of detection and transformants that lose the vector will not exhibit this phenotype. Thus, the vectors of the present invention can stabilize and maintain any DNA sequence of interest.

The cloning vectors and transformants of the present invention provide for the cloning of genes to improve yields of various products that are currently produced in Streptomyces and related cells. Examples of such products include, but are not limited to, streptomycin, tylosin, cephalosporins, actaplanin, avoparcin, narasin, monensin, apramycin, tobramycin, erythromycin, tetracycline, chloramphenicol, vancomycin, teichomycin, and the like. The present invention also provides selectable vectors that are useful for cloning, characterizing, and reconstructing DNA sequences that code for commercially important proteins such as, for example, human insulin, human proinsulin, glucagon, interferon, human growth hormone, avian growth hormone, bovine growth hormone, porcine growth hormone, interleukin I, interleukin II, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, streptomycin, cephalosporins, tylosin, actaplanin, avoparcin, narasin, monensin, apramycin, tobramycin, tetracycline, chloramphenicol, erythromycin, teichomycin, and vancomycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

*Escherichia coli* K12 HB101/pFJ301 (NRRL B-15724) can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

*E. coli* K12 HB101/pFJ301 can be grown under aerobic culture conditions over a relatively wide pH range of about 6.5 to 8 at temperatures ranging from about 25° to 40° C. For the production of plasmid pFJ301 in the greatest quantity, however, it is desirable to start with a culture medium at a pH of about 7.2 and maintain a culture temperature of about 37° C. Culturing the *E. coli* cells under the aforementioned conditions results in a reservoir of cells from which the plasmids are respectively isolated by techniques well known in the art.

The following examples further illustrate and detail the invention disclosed herein. Both an explanation of and the actual procedures for constructing the invention are described where appropriate.

EXAMPLE 1

Culture of *E. coli* K12 HB101/pFJ301 and Isolation of Plasmid pFJ301

The bacterium *E. coli* K12 HB101/pFJ301 (NRRL B-15724) is cultured in LB medium which contains, per liter aqueous solution, 10 g. Bacto tryptone, 5 g. Bacto yeast extract and 10 g. NaCl (pH 7.5) with 25 µg./ml. each of the antibiotics ampicillin and chloramphenicol according to conventional microbiological procedures. After 18 hours incubation, about 0.5 ml. of the culture is transferred to a 1.5 ml. Eppendorf tube and centrifuged for about 15 seconds. Unless otherwise indicated, all the manipulations are done at ambient temperature. The resultant supernatant is carefully removed with a fine-tip aspirator and the cell pellet is suspended in about 100 µℓ of freshly prepared lysozyme solution which contains 2 µg./ml. lysozyme, 50 mM glucose, 10 mM EDTA and 25 mM Tris-HCl (pH 8). After incubation at 0° C. for 30 minutes, about 200 µl. of alkaline SDS (sodium dodecyl sulfate) solution (0.2N NaOH, 1% SDS) is added and the tube gently vortexed and then maintained at 0° C. for 5 minutes. Next, about 150 µℓ of 3M sodium acetate is added and the contents of the tube are mixed gently by inversion for a few seconds.

The tube is maintained at 0° C. for 60 minutes and then centrifuged for 20 minutes at 15,000 rpm to yield an almost clear supernatant. The supernatant is transferred to a second centrifuge tube and the DNA is extracted with phenol:chloroform (50:50) and chloroform: isoamyl alcohol (24:1). Two volumes of cold ethanol are then added to the aqueous phase to precipitate the DNA. The DNA precipitate is obtained by centrifugation. The DNA is raised in 1 ml. of 1/10 TE (1mM Tris-HCl, pH8; 0.1mM EDTA).

EXAMPLE 2

Construction of Plasmid pFJ269

A. BamHI Digestion of Plasmid pFJ301 and Isolation of the ~8.8 kb Origin of Replication-Containing Restriction Fragment About 20 µl. (20 µg.) of plasmid pFJ301 DNA, 5 µl. BSA(Bovine Serum albumin, 1 mg./ml.), 19 µl. water, 1 µl. of BamHI (containing 3 New England Bio Labs units) restriction enzyme*, and 5 µl. reaction mix** are incubated at 37° C. for 2 hours. The reaction is terminated by the addition of about 50 µl. of 4M ammonium acetate and 200 µl. of 95% ethanol. The mixture is cooled to −20° C. for about 18 hours to precipitate the DNA. The resultant DNA precipitate is collected by centrifugation and the desired ~8.8 kb BamHI fragments are separated and isolated conventionally by agarose gel electrophoresis in substantial accordance with the teaching of Maniatis et al., 1982 Molecular Cloning, Cold Spring Harbor Laboratories, Cold Spring Harbor, N.Y. Following isolation, the fragment is resuspended in about 20 µl. of 1/10 TE buffer for subsequent ligation.

*Restriction enzymes and instructions can be obtained from the following sources:

New England Bio Labs., Inc.
32 Tozer Road
Beverly, Mass. 01915
Boehringer-Mannheim Biochemicals
7941 Castleway Drive
P.O. Box 50816
Indianapolis, Ind. 46250

Bethesda Research Laboratories Inc.
8717 Grovemont Circle
P.O Box 577
Gaithersburg, Md. 20760

**Reaction mix for BamHI restriction enzyme was prepared with the following composition.

1.5M NaCl
60mM Tris-HCl, pH 7.9
60mM MgCl₂

B. Digestion and Isolation of the ~1.6 kb BamHI Fragment of Plasmid pLR2

The desired digestion was carried out in substantial accordance with the teaching of Example 2A above except that plasmid pLR2, the construction of which is disclosed in U.S. Pat. No. 4,416,994 and incorporated herein by reference, was used in place of plasmid pFJ301. The resulting 1.6 kb BamHI fragments were separated and isolated conventionally by agarose gel electrophoresis (Maniatis et al., 1982).

C. Ligation

About 20 µl. of BamHI treated plasmid pFJ301 (from Example 2A), 20 µl. of BamHI treated plasmid pLR2 (from Example 2B), 5 µl. BSA (1 mg./ml.), 1 µl. of T4 DNA ligase*, and 5 µl. ligation mix** were incubated at 16° C. for 4 hours. The reaction was terminated by precipitation with ethanol at −20° C. The resultant DNA precipitate was washed twice in 70% ethanol, dried in vacuo and suspended in about 50 µl. of P medium (Hopwood and Wright, 1978, J. Molecular and General Genetics 162:307) for subsequent transformation.

*T4 DNA ligase can be obtained from the following sources:

New England Bio Labs., Inc.
32 Tozer Road

Beverly, Mass. 01915

Bethesda Research Laboratories
P.O. Box 577
Gaithersburg, Md. 20760

Boehringer-Mannheim Biochemicals
7941 Castleway Drive
P.O. Box 50816
Indianapolis, Ind. 46250

**Ligation mix was prepared with the following composition.

500 mM Tris-HCl, pH 7.8
200 mM Dithiothreitol
100 mM MgCl$_2$
10 mM ATP

Recombinant plasmids of two orientations can be produced because the ~1.6 kb BamHI resistance-conferring fragment can be oriented in either direction. A restriction site and functional map of plasmids pFJ269 and pFJ305 is presented in FIG. 3 of the accompanying drawings. Those skilled in the art will recognize and understand that additional recombinant plasmids containing the ~8.8 kb BamHI origin of replication-containing fragments can be generated by the above procedure. These plasmids are functional and thus further exemplify the present invention. The aforementioned plasmids can be conventionally transformed and then identified by restriction enzyme and gel electrophoretic analysis.

For future ease of comprehension, derivative plasmid constructions will be exemplified using plasmid pFJ269, wherein the thiostrepton resistance-conferring fragment is oriented such that the unique ClaI restriction site is nearest to the BclI restriction site of the 8.8 kb BamHI restriction fragment. However, derivative plasmids of plasmid pFJ305 can also be constructed in accordance with the teaching of the examples disclosed herein.

EXAMPLE 3

Construction of *Streptomyces ambofaciens*/pFJ269 and *S. ambofaciens*/pFJ305

About 1 µg. of the DNA from Example 2C and 100 µl. of protoplasts of *Streptomyces ambofaciens*, a strain deposited and made part of the permanent stock culture collection of the Northern Regional Research Laboratory, Peoria, Illinois, from which it is available to the public under the accession number NRRL 2420, were mixed with 0.5 ml. 20% PEG (polyethylene glycol) in P medium. After 2-3 minutes at ambient temperature 4 ml. of P medium was added to the mixture and centrifuged (about 5 mins., 4° C., 15,000 rpm). The pellet was resuspended in 1 ml. of P medium and 100 µl. of the suspension was plated on fresh or dried R2 plates and incubated for 16-24 hours at 30° C. The desired transformants were selected for thiostrepton resistance by overlaying the regenerating protoplasts with R2 medium (Hopwood et al., 1978) top agar containing sufficient thiostrepton to bring the final plate concentration to 50 µg./ml. The resultant *Streptomyces ambofaciens*/pFJ269 and *S. ambofaciens*/pFJ305 thiostrepton resistant colonies were isolated according to known procedures, cultured, and then conventionally identified by restriction enzyme and agarose gel electrophoretic analysis of the constitutive plasmids (Maniatis et al., 1982). The transformant cultures are then used for subsequent production and isolation of their respective plasmids.

EXAMPLE 4

Construction of Plasmids pFJ306 and pFJ307

A. Partial BamHI Digestion of Plasmid pFJ269

About 10 µl. (10 µg.) of plasmid pFJ269, 5 µl. BSA (1 mg./ml.), 29 µl. water, 1 µl. of BamHI (diluted 1:4 with water) restriction enzyme, and 5 µl. reaction mix are incubated at 37° C. for 15 minutes. The reaction is terminated by the addition of about 50 µl. of 4M ammonium acetate and 200 µl. of 95% ethanol. The resultant DNA precipitate is washed twice in 70% ethanol, dried in vacuo, and suspended in 20 µl. water.

Plasmid pFJ269 contains two nonessential BamHI restriction sites flanking the ~1.6 kb thiostrepton resistance marker. Since both sites are nonessential for DNA replication, either one is available for restriction purposes. Those skilled in the art will recognize and understand that partial digestions can be performed such that plasmid pFJ269 may be cleaved at one of these two restriction sites; the preferred fragment cleavage can be isolated according to conventional restriction mapping analysis. In this example, plasmid pFJ269 DNA is first cleaved at the BamHI restriction site that is adjacent to the PvuII restriction site located within the thiostrepton resistance marker and subsequently isolated and suspended in 20 µl. of 1/10 TE buffer for ligation.

B. Isolation of the ~1.5 kb BclI Tyrosinase Gene Fragment of Plasmid pIJ702

About 20 µl. (20 µg.) of plasmid pIJ702 DNA (ATCC 39155), 10 µl. BSA (1 mg./ml.), 55 µl. water, 5 µl. of BclI restriction enzyme, and 10 µl. reaction mix* are incubated at 50° C. for 4 hours. The reaction is terminated by precipitation with ethanol. The DNA is pelleted, dried and resuspended in 50 µl. of 1/10 TE.
*Reaction mix for BclI restriction enzyme was prepared with the following composition.

750 mM KCl
60 mM Tris-HCl, pH 7.4 at 25° C.
100 mM MgCl$_2$
10 mM Dithiothreitol C. Ligation The desired construction is conveniently done by adding the partial BamHI digested fragment of Example 4A to the ~1.5 kb BclI digested tyrosinase gene fragment isolated above by use of T4 DNA ligase. Ligation is performed in substantial accordance with the teaching of Example 2C. The tyrosinase gene fragment, as previously discussed with the antibiotic resistance-containing fragments, can also be ligated in either orientation to the plasmid pFJ301 origin of replication-containing fragment. This possibility of dual orientation, in conjunction with the availability of two nonessential BamHI restriction sites can generate four new plasmids: pFJ306, pFJ307, pFJ308, and pFJ309. A restriction site and functional map of plasmids pFJ306 and pFJ307 is presented in FIG. 4 of the accompanying drawings.

EXAMPLE 5

Construction of *Streptomyces ambofaciens*/pFJ306 and *S. ambofaciens*/pFJ307

The desired constructions can be made in substantial accordance with the teaching of Example 3 except that plasmids pFJ306 and pFJ307, rather than plasmids pFJ269 or pFJ305, are used for the transformation. The resulting transformants are selected for thiostrepton resistance by the method described in Example 3 above and additionally selected for the resulting mel+ phenotype. The resultant *Streptomyces ambofaciens*/pFJ306 and *S. ambofaciens*/pFJ307 colonies are isolated according to known procedures and then conventionally identified by restriction enzyme and electrophoretic analysis of the constitutive plasmids.

EXAMPLE 6

Construction of Plasmids pFJ310 and pFJ311

A. Partial BclI Digestion of Plasmid pFJ306 and Ligation to the ~3.4 kb BamHI Neomycin Resistance-Conferring Fragment of Plasmid pLR1

The desired digestion is carried out in substantial accordance with the teaching of Example 4A except that plasmid pFJ306 and BclI restriction enzyme are used in place of plasmid pFJ269 and BamHI restriction enzyme and the reaction is carried out at 50° C. Plasmid pFJ306 contains two nonessential BclI restriction sites flanking the thiostrepton resistance marker which are available for inserting another genetic marker in the plasmid. Thus, as discussed in Example 4C, cloning the ~3.4 kb BamHI neomycin resistance-conferring fragment of plasmid pLR1, the construction of which is disclosed in U.S. Pat. No. 4,416,994 and incorporated herein by reference, into plasmid pFJ306 (which carries thiostrepton resistance and confers melanin production on its host) generates the four new plasmids pFJ310, pFJ311, pFJ312, and pFJ313. A restriction site and functional map of plasmids pFJ310 and pFJ311 is presented in FIG. 5 of the accompanying drawings.

EXAMPLE 7

Construction of *Streptomyces ambofaciens*/pFJ310 and *S. ambofaciens*/pFJ311

The transformant *S. ambofaciens*/pFJ310 and *ambofaciens*/pFJ311 is made in substantial accordance with the teaching of Example 5, with the exception that plasmids pFJ310 and pFJ311, rather than plasmids pFJ269 or pFJ305, are used for the transformation. The desired transformant is selected for thiostrepton resistance by overlaying the regenerating protoplasts with R2 medium top agar containing sufficient thiostrepton to bring the final plate concentration to 50 μg./ml and sufficient neomycin to bring the final plate concentration to 2 μg./ml. The resultant *Streptomyces ambofaciens*/pFJ310 and *S. ambofaciens*/pFJ311 thiostrepton and neomycin resistant colonies are isolated according to known procedures and then conventionally identified by restriction enzyme and electrophoretic analysis of the constitutive plasmids.

EXAMPLE 8

Construction of Plasmid pFJ314 and *Streptomyces ambofaciens*/pFJ314

A. BamHI Partial Digestion of Plasmid pFJ310

The desired digestion is carried out in substantial accordance with the teaching of Example 4A except that plasmid pFJ310 is used in place of plasmid pFJ269.

B. BclI Partial Digestion of BamHI Partially Digested Plasmid pFJ310 and Isolation of Digested DNA The desired digestion is carried out in substantial accordance with the teaching of Example 8A except that BclI is used in place of BamHI and partially digested plasmid pFJ310 of Example 8A is used in place of Plasmid pFJ269. In addition, the reaction is carried out at 50° C.

The desired fragment (a fragment of DNA identical to that of plasmid pFJ310 and pFJ311 except that the ~0.5 kb BamHI-BclI fragment is deleted) is isolated conventionally by agarose gel electrophoresis (Maniatis, et al., 1982) and resuspended in about 20 μl. of 1/10 TE buffer for subsequent ligation.

C. Self Ligation of Partially Digested DNA from Example 8B

The desired ligation is carried out in substantial accordance with Example 2C except that the partially digested DNA isolated in Example 8B is used in place of BamHI treated pFJ301 and BamHI treated pLR2. Because BamHI and BclI sticky ends are identical and because the DNA isolated in Example 8B has such ends, the ends of this DNA can be ligated to form circular plasmid DNA. The suspended DNA constitutes the desired plasmid pFJ314. A restriction site and functional map is presented in FIG. 6 of the accompanying drawings.

The transformant *S. ambofaciens*/pFJ314 is made in substantial accordance with the teaching of Example 3, with the exception that plasmid pFJ314, rather than plasmids pFJ269 or pFJ305, is used for the transformation. The desired transformant is selected for thiostrepton resistance and neomycin resistance by overlaying the regenerating protoplasts with R2 medium top agar containing sufficient thiostrepton to bring the final plate concentration to 50 μg./ml and sufficient neomycin to bring the final plate concentration to 2 μg./ml. The resultant *Streptomyces ambofaciens*/pFJ314 thiostrepton and neomycin resistant colonies are isolated according to known procedures and then conventionally identified by restriction enzyme and electrophoretic analysis of the constitutive plasmids.

EXAMPLE 9

Construction of Plasmids pFJ315 and pFJ316

A. BamHI Digestion of Plasmid pFJ306 and Plasmid pBR328

The desired digestions are carried out in substantial accordance with Example 2A except that plasmids pFJ306 and pBR328 are used, in separate reactions, in place of plasmid pFJ301.

B. Ligation of BamHI Digested Plasmid pFJ306 and BamHI Digested pBR328

The desired ligation is carried out in substantial accordance with Example 2C except that the BamHI treated plasmids pFJ306 and pBR328 are used in place of BamHI treated plasmids pFJ301 and pLR2. The suspended DNA constitutes the desired plasmids pFJ315 and pFJ316. Recombinant plasmids of two orientations result because the restricted plasmid pBR328 can be oriented in either direction. A restriction site and functional map of each of plasmids pFJ315 and pFJ316 is presented in FIG. 7 of the accompanying drawings.

EXAMPLE 10

Construction of *E. coli* K12 HB101/pFJ315 and *E. coli* K12 HB101/pFJ316

About 1 ml. of frozen competent *E. coli* K12 HB101 cells (Bolivar et al., 1977, Gene 2:75–93) are brought to 0° C.

Plasmids pFJ315 and pFJ316 in TE buffer (prepared in Example 9B) are ethanol precipitated, suspended in 50 μl. of 30mM calcium chloride solution, and gently mixed in a test tube with about 100 μl. of competent *E. coli* K12 HB101 cells. The resultant mixture is incubated on ice for about 45 minutes and then at 42° C. for about 1 minute. Next, about 3 ml. of L-broth (Bertani, 1951, J. Bacteriology 62:293) containing 50 μg./ml. of ampicillin is added. The mixture is incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies are first selected, and tested for the expected phenotype ($Amp^R$, $Cm^R$, $Tet^S$), and then conventionally identified as the desired *E. coli* K12 HB101/pFJ315 and *E. coli* K12 HB101/pFJ316 transformants by restriction enzyme and gel electrophoretic analysis of the constitutive plasmids.

EXAMPLE 11

Construction of *Streptomyces ambofaciens*/pFJ315 and *S. ambofaciens*/pFJ316

The desired constructions are made in substantial accordance with the teaching of Example 3 with the exception that plasmids pFJ315 and pFJ316 rather than plasmids pFJ269 or pFJ305 are used for the transformation. The resulting transformants are selected for thiostrepton resistance by the method described in Example 3 above. The thus constructed thiostrepton resistant *Streptomyces ambofaciens*/pFJ315 and *S. ambofaciens*/pFJ316 colonies are isolated according to known procedures and then conventionally identified by restriction enzyme and electrophoretic analysis of the constitutive plasmids.

EXAMPLE 12

Construction of Plasmid pFJ317 and Transformants *S. ambofaciens*/pFJ317 and *E. coli* K12 HB101/pFJ317

Most *E. coli* K12 strains methylate certain residues in their DNA. For example, a methylase specified by the dam gene methylates at the N6 position of the indicated adenine in the DNA sequence $5'GA^{me}TC3'$. This methylation has been shown to interfere with cleavage of DNA by some (but not all) restriction endonucleases whose recognition sequences comprise or include the methylated sequences. BclI, a restriction enzyme commonly used in this invention, will not cleave the BclI recognition sequence $5'TGATCA3'$ if it has been methylated. To avoid this problem, plasmid pFJ301 should be transferred to an *E. coli dam*⁻ strain such as GM48, a strain deposited and made part of the permanent stock culture collection of the Northern Regional Research Laboratory, Peoria, Ill. The strain is available to the public under the accession number NRRL B-15725.

A. BamHI Partial Digestion of Plasmid pFJ315

The desired digestion is carried out in substantial accordance with the teaching of Example 8A except that plasmid pFJ315 is used in place of plasmid pFJ310.

B. BclI Partial Digestion of BamHI Partially Digested Plasmid pFJ315 and Isolation of Digested DNA The desired digestion and isolation is carried out in substantial accordance with the teaching of Example 8B except that plasmid pFJ315 is used in place of plasmid pFJ310.

C. Self Ligation of Partially Digested DNA from Example 12B

Ligation is performed in substantial accordance with the teaching of Example 8C with the exception that plasmid pFJ315 DNA is used rather than plasmid pFJ310 DNA. The resulting plasmid pFJ317 is useful because it contains only one BamHI restriction site and therefore provides a unique site for subsequent restriction. A restriction site and functional map of plasmid pFJ317 is presented in FIG. 8 of the accompanying drawings.

D. Construction of *E. coli* K12 HB101/pFJ317

The *E. coli* K12 HB101/pFJ317 construction is made in substantial accordance with the teaching of Example 10 with the exception that plasmid pFJ317, rather than plasmids pFJ315 and pFJ316, is used for the transformation.

E. Construction of *S. ambofaciens*/pFJ317

The *S. ambofaciens*/pFJ317 construction is made in substantial accordance with the teaching of Example 3 with the exception that plasmid pFJ317, rather than plasmids pFJ269 or pFJ305, is used for the transformation.

EXAMPLE 13

Construction of Plasmids pFJ318 and pFJ319 and Transformants *Streptomyces ambofaciens*/pFJ318, *S. ambofaciens*/pFJ319, *E.coli* K12 HB101/pFJ318 and *E. coli* K12 HB101/pFJ319

A. BamHI Partial Digestion of Plasmid pFJ310

The desired digestion is carried out in substantial accordance with the teaching of Example 8A.

B. BclI Partial Digestion of BamHI Partially Digested Plasmid pFJ310 and Isolation of Digested DNA The desired digestion and isolation is carried out in substantial accordance with the teaching of Example 8B.

C. BamHI Digestion of Plasmid pBR328

The desired digestion is carried out in substantial accordance with the teaching of Example 9A except that only plasmid pBR328 was digested.

D. Ligation of BamHI Digested Plasmid pBR328 to DNA Isolated from Example 13B and Selection of Cultures Carrying Plasmids pFJ318 and pFJ319

The desired ligation and selections are carried out in substantial accordance with example 9B except that the DNA isolated in Example 13B is used in place of the BamHI treated pFJ306. A restriction site and functional map of plasmid pFJ318 and pFJ319 is presented in FIG. 9 of the accompanying drawings.

E. Construction of S. ambofaciens/pFJ318 and S. ambofaciens/pFJ319

The S. ambofaciens/pFJ318 and S. ambofaciens/pFJ319 are made in substantial accordance with the teaching of Example 3 with the exception that plasmids pFJ318 and pFJ319, rather than plasmid pFJ269 or pFJ305, are used for the transformation.

F. Construction of E. coli K12 HB101/pFJ318 and E. coli K12 HB101/pFJ319

The E. coli K12 HB101/pFJ318 and E. coli K12 HB101/pFJ319 are made in substantial accordance with the teaching of Example 10 with the exception that plasmids pFJ318 and pFJ319, rather than plasmids pFJ315 and pFJ316, are used for the transformation.

Representative transformants constructed in accordance with the foregoing teaching include the following listed in Table 1 below.

Table 1
Representative Transformants

1. Streptomyces R/R$^1$ wherein R is ambofaciens, aureofaciens, griseofuscus, fradiae*, lividans, cinnamonensis or toyocaensis and wherein R$^1$ independently is a plasmid from the group consisting of pFJ269, pFJ305, pFJ306, pFJ307, pFJ308, pFJ309, pFJ310, pFJ311, pFJ312, pFJ313, pFJ314, pFJ315, pFJ316, pFJ317, pFJ318, and pFJ319.

*The following procedure is used for transforming S. fradiae. Use low OD cells (less than 4 O.D. units) grown at 29° C. in the presence of 0.4% glycine in TSB medium. Protoplasts are formed in the presence of 1 mg./ml. lysozyme in P medium on ice followed by two washes with P medium. Chill for 1-3 hours and then warm to ambient temperature.

Mix 0.8 μg. calf thymus DNA and 1.5 μg. protamine sulfate for one minute, then add: purified plasmid DNA (less than 100 ng) suspended in 10 μl. of P medium, 200 μl. of diluted protoplasts (1/3x), 0.9 ml. of 55% PEG 1000 and mix for one minute. Using soft agar overlays, plate protoplasts and incubate at 29° C. for 16-24 hours then overlay with the appropriate antibiotic. Reincubate at 29° C. and score the plates in 7-10 days.

We claim:

1. A recombinant DNA cloning vector comprising:
   (a) a functional Streptomyces origin of replication-containing restriction fragment derived from the ~8.8 kb BamHI restriction fragment of plasmid pFJ301, and
   (b) one or more DNA segments that convey resistance to at least one antibiotic or that convey colorimetric selectivity when transformed into a sensitive restrictionless host cell.

2. The cloning vector of claim 1 wherein the restriction fragment of pFJ301 is the ~8.8 kb BamHI restriction fragment.

3. The recombinant DNA cloning vector of claim 1 selected from the group consisting of plasmids pFJ269, pFJ305, pFJ306, pFJ307, pFJ308, pFJ309, pFJ310, pFJ311, pFJ312, pFJ313, and pFJ314.

4. The cloning vector of claim 3 which is plasmid pFJ269.

5. The cloning vector of claim 3 which is plasmid pFJ305.

6. A transformed restrictionless host cell comprising a recombinant DNA cloning vector of claim 1.

7. The transformed host cell of claim 6 which is Streptomyces.

8. The transformed host cell of claim 6 in which the recombinant DNA cloning vector is selected from the group consisting of plasmids pFJ269, pFJ305, pFJ306, pFJ307, pFJ308, pFJ309, pFJ310, pFJ311, pFJ312, pFJ313, and pFJ314.

9. The transformed host cell of claim 8 which is restrictionless Streptomyces.

10. The transformed Streptomyces of claim 9 which is Streptomyces fradiae.

11. The transformed Streptomyces of claim 9 which is Streptomyces griseofuscus.

12. The transformed Streptomyces of claim 9 which is Streptomyces coelicolor.

13. The transformed Streptomyces of claim 9 which is Streptomyces ambofaciens.

14. The transformed host cell of claim 9 which is Streptomyces ambofaciens/pFJ269.

15. A recombinant DNA cloning vector of claim 1 comprising in addition:
    (c) a functional replicon-containing fragment of an E. coli plasmid.

16. The recombinant DNA cloning vector of claim 15 wherein the functional replicon-containing fragment of the E. coli plasmid is selected from the group consisting of replicon-containing fragments of plasmids pBR322, pBR325, and pBR328.

17. The recombinant DNA cloning vector of claim 15 which is selected from the group consisting of plasmids pFJ315, pFJ316, pFJ317, pFJ318, and pFJ319.

18. A transformed restrictionless host cell comprising a recombinant DNA cloning vector of claim 17.

19. A transformed restrictionless host cell which is Streptomyces R/R' wherein R is ambofaciens, fradiae, griseofuscus, lividans, aureofaciens, cinnamonensis, or toyocaensis and wherein R' independently is a recombinant DNA cloning vector of claim 3.

20. A DNA molecule consisting essentially of the ~8.8 kb BamHI restriction fragment of plasmid pFJ301.

* * * * *